(12) United States Patent
LePivert (10) Patent No.: US 6,551,309 B1
(45) Date of Patent: Apr. 22, 2003

(54) DUAL ACTION CRYOPROBE AND METHODS OF USING THE SAME

(75) Inventor: Patrick J. M. LePivert, Jupiter, FL (US)

(73) Assignee: Cryoflex, Inc., FL (US)

( * ) Notice: Subject to any disclaimer, the term of this patent is extended or adjusted under 35 U.S.C. 154(b) by 132 days.

(21) Appl. No.: 09/662,213

(22) Filed: Sep. 14, 2000

(51) Int. Cl.⁷ ............................................. A61B 18/18
(52) U.S. Cl. .......................... 606/20; 606/21; 606/23; 606/24
(58) Field of Search ..................... 606/20, 21, 22, 606/23, 24, 25, 26

(56) References Cited

U.S. PATENT DOCUMENTS

| | | | |
|---|---|---|---|
| 2,269,018 A | 1/1942 | Guignon, Jr. | |
| 3,292,331 A | 12/1966 | Sams | |
| 3,534,739 A | 10/1970 | Byrne | |
| 3,755,982 A | 9/1973 | Schmidt | |
| 3,782,049 A | 1/1974 | Sachs | |
| 3,823,718 A | 7/1974 | Tromovitch | |
| 4,082,096 A * | 4/1978 | Benson | 606/21 |
| 4,211,231 A | 7/1980 | Rzasa | |
| 4,229,497 A | 10/1980 | Piazza | |
| 4,641,468 A | 2/1987 | Slater | |
| 4,770,171 A * | 9/1988 | Sweren et al. | 606/25 |
| 4,774,794 A | 10/1988 | Grieb | |
| 5,069,223 A | 12/1991 | McRae | |
| 5,123,222 A | 6/1992 | Guarriello et al. | |
| 5,231,813 A | 8/1993 | Drawdy | |
| 5,281,215 A * | 1/1994 | Milder | 606/20 |
| 5,324,286 A * | 6/1994 | Fowle | 606/20 |
| 5,423,807 A * | 6/1995 | Milder | 606/20 |
| 5,566,521 A | 10/1996 | Andrews et al. | |
| 5,771,649 A | 6/1998 | Zweig | |
| 5,800,488 A * | 9/1998 | Crockett | 128/DIG. 27 |
| 5,846,235 A * | 12/1998 | Pasricha et al. | 606/20 |
| 5,899,899 A * | 5/1999 | Arless et al. | 606/20 |
| 5,902,299 A * | 5/1999 | Jayaraman | 604/101.05 |
| 6,027,499 A * | 2/2000 | Johnston et al. | 600/104 |
| 6,051,019 A * | 4/2000 | Dobak, III | 606/20 |
| 6,235,019 B1 * | 5/2001 | Lehmann et al. | 606/20 |
| 6,270,493 B1 * | 8/2001 | Lalonde et al. | 606/23 |
| 6,350,276 B1 * | 2/2002 | Knowlton | 607/101 |

FOREIGN PATENT DOCUMENTS

FR 767681 3/1999

* cited by examiner

Primary Examiner—Michael Peffley
(74) Attorney, Agent, or Firm—McHale & Slavin PA (57) ABSTRACT

Cryosurgery is performed with cryosurgical probe tips either contacting the tissue or by tips which deliver refrigerant onto the tissue. A dual action probe tip can be used to perform either operation separately or may be used for application of both methods. Various method steps define the procedures for use of the probe tips.

29 Claims, 8 Drawing Sheets

DUAL ACTION CRYOPROBE AND METHODS OF USING THE SAME

FIELD OF THE INVENTION

The present invention relates to a design and construction of a cryoprobe tip for freezing tissues. In particular, the present invention relates to a specific cryoprobe tip configuration and methods of application allowing an improved application of refrigerant that combines direct (spray) and indirect (closed tip) contact of the selected refrigerant with the target tissue in a timely manner. Also, the present invention provides a plurality of interchangeable tips for a better adaptation to the tissue configuration and location.

BACKGROUND OF THE INVENTION

Cryosurgery is a well-established surgical method which is useful in the treatment of many conditions and which involves the application of extreme cold to tissues to effect freezing of the tissues. The instruments used are, in general, of two types. In the spray tip, the refrigerant is sprayed directly onto the tissue to be frozen. In the closed tip, the cryogenic fluid is confined within the tip. The refrigerant is delivered to a portion of the tip that is inserted into the tissue. Selection of a particular instrument depends on multiple parameters among which are location and volume of the lesion, cost-efficiency ease of application, time spent on application and predictability of freezing effects.

The closed tip probe may use a low boiling point refrigerant like liquid Nitrogen ($LN_2$) or Joule Thomson expansion of fluids like Nitrous Oxide ($N_2O$) or Carbon Dioxide ($CO_2$), or Argon gas. Other techniques include using the latent heat of vaporization, as with Freon, or precooled gas and liquids. Exemplary liquids include chlorodifluoromethane, polydimethylsiloxane, ethyl alcohol, HFC's such as AZ (50-50 mixture of difluoromethane and pentafluoroethane, sold by Allied Signal), and CFCs such as DuPont's Freon. The cold generated by a cryogenic fluid is confined to the area of the probe tip where heat transfer occurs across the tip to the surrounding tissues to form an ice ball of frozen tissue. This method has the advantage of locating the frozen zone more precisely and permitting interstitial freezing of tissues by inserting the probe tip deep into the tissue.

But the main drawbacks are that the probe tip usually does not reach the lowest temperature permitted by the refrigerant, due to the less effective heat conductivity of the tip material, forcing the operator to use low boiling point refrigerants. Using these refrigerants requires changing the probe location within the tissue and/or using multiple probes simultaneously to complete the freezing process if a target tissue is more than a few cubic centimeters. Also the miniaturization of modern instruments required by the endoscopic or catheter-based applications requires safe, quick, and efficient cryoprobes which are very small and flexible.

Other drawbacks are that these systems are often bulky and not easily movable from one location to the other, nor are they well suited to use outside of a formal operating room or in minor surgical procedures due to their cost and maintenance requirements.

In contrast, open end, or spray type tips commonly used are less expensive and disposable hand held systems. Advantages of the spray technique are the higher thermal efficiency and the capability of covering a larger area than the closed tip cryoprobe. The tips are used generally for superficial and/or external cryotreatments. Examples of these types of systems include U.S. Pat. No. 3,534,739 to Bryne and U.S. Pat. No. 3,823,718 to Tromovitch. Such devices apply the refrigerant directly to the tissue via a spray nozzle without any contact of the tip with the tissue.

Usually, the operator estimates the effect of cryosurgery by the appearance of tissue as it freezes. At times, when facing large or malignant lesions the operator uses invasive monitoring techniques of the freezing effects using thermocouple or impedance needles inserted into the target tissue, which are not practicable or desirable everywhere. Such devices are potentially hazardous because of the risk of spreading malignant cells. Noninvasive monitoring may be employed, including X-ray, CT, Ultrasonography, or MRI. U.S. Pat. No. 5,069,223 discloses several electrodes/sensors which may be used to evaluate freezing effects in tissue.

The procedure of the simple viewing of the frozen tissue via an endoscope has been recently advocated as a method of application of cryosurgery. U.S. Pat. No. 5,846,235 describes such an endoscopic application using this very unreliable method of monitoring. However, spray tips are not suitable for use in procedures performed within the body due to the difficulty in controlling the amount of cryogen released and the effects of overspray on surrounding tissues.

SUMMARY OF THE INVENTION

The prior art is lacking any suggestion of a cryosurgical probe or group of probes with the capability of being used during the same operation to the same tissue, in a dual action mode, i.e. as a closed end and a spray tip type probe. U.S. Pat. No. 4,211,231 describes interchangeable cryotips for successive applications of the different modes of freezing.

Also absent in the prior art is any suggestion that such a system can be used in interstitial freezing of tissues. The reason is that interstitial expansion of gas or liquid refrigerant could be harmful to tissues by forcing gas bubbles under pressure into the tissue with the risk of inflating it or embolizing an open vessel. Our invention avoids this risk by a two-steps method of freezing the tissues using a dual action mode.

Moreover, there is no reference to the use of $N_2O$, or $CO_2$ as particularly suited for the treatment of malignancies, with the exception of some palliative treatments, or on masses of tissue larger than a few cubic centimeters. The usual procedure is to treat these lesions with $LN_2$, Argon, or other powerful refrigerants, such as gas mixtures in cryocoolers with mono or multiprobe systems.

Also absent in the prior art is the regulation of flow of refrigerant in the spray tip type probe and electrical monitoring of the ice ball, which is effected in our invention by an electrical method as described in U.S. patent application Ser. No. 09/429,810 entitled Method and Apparatus for Monitoring Cryosurgical Operations filed Oct. 29, 1999 incorporated herein by reference, also referred to as Cryosurgical Imaging System (CIS).

Another major feature of this invention is that such a contact spray technique solves two main issues in cryosurgery:

a. the alleged need of powerful refrigerant for treating malignant tumors and the temperature needed for destruction of tissues, normal, benign, or malignant, and b. the necessary use of powerful refrigerants, such as $LN_2$, Argon gas, or mixed refrigerant, in very small closed-end probes, under 3 mm in outer diameter, to get sufficient power efficiency. These small probes are more and more in use every day due to the rapid expansion of endoscopic, percutaneous and minimally invasive surgical procedures.

Conventionally, powerful refrigerants were thought necessary because of the demonstrated effectiveness of fast freezing and large ice ball created by higher thermal gradients. Recently, Rubinsky and Degg, Proc., R. soc. Lond. B234, 343–358 (1988), have shed new light on the process of freezing in tissue. The results show that tissue can be destroyed by freezing to temperature as high as –2 degrees C., and that conventional temperatures as low as –50 degrees C. are not required for tissue destruction, if the freezing process is done in such a manner as to insure destruction of the vasculature network.

These findings tend to suggest the use of slower freezing techniques, thus the possible use of medium powered refrigerants, like $N_2O$, and they focus the monitoring more on the vascular bed modifications than through the direct or indirect cell alterations. A real time monitoring of vascular freezing, whatever is the nature of the target tissue is precisely the result obtained by the use of one embodiment of our invention. A recent experimental study ("Bioelectrical impedance Imaging for monitoring cryosurgery", Presentation to the first European Congress of Cryosurgery, San Sebastian, Spain, 30th Mar. 2 Apr. 6, 2000, P. Le Pivert et al.) confirms the existence of different destructive temperature for different tissues, and cryonecrosis at temperature higher than the usually recommended –50 degrees C. It confirms also the efficacy of complex impedance measurements to predict the extent of electrical modifications of frozen tissues related to vascular obliteration and to delayed cryonecrosis.

There remains a need for an alternative means of topical or interstitial application of cryosurgery for the treatment such as hemostasis, ablation, or other cryotreatment of healthy or diseased tissues, having the following characteristics:

1) An ability to be used in contact with the tissue over a larger area than normally available with a usual closed end tip probe using the same refrigerant;
2) An ability to safely fulfill the required task whether it is hemostasis, ablation, or other cryotreatments;
3) Affordability; and
4) Technique simplicity.

It is thus an objective of the invention to provide an alternate improved cryotip system, which combines the advantages of the closed end and open-end techniques, in surface and/or in interstitial applications of cryosurgery, and characterized in that it fulfills most if not all of the criteria noted above.

It is a further objective to provide different refrigerant and different refrigerant sources to connect with such a closed (contact)-open (spray) end tip system.

It is a further objective to provide different methods of application of such a contact-spray tip cryoprobe for different types of tissue—benign or malignant—and different tissue location within the body.

And it is still a another objective to provide a complete cryosurgical system using $N_2O$ or $CO_2$ as the refrigerant, a Joule-Thomson effect into the cryotip, and an electrical monitoring system allowing control of the efficacy, in real time, of the probe, or group of probes and the optimal flow rate of gas/liquid mixture into the expansion chamber of the contact-spray tip.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DESCRIPTION OF THE DRAWINGS

Figure 1:
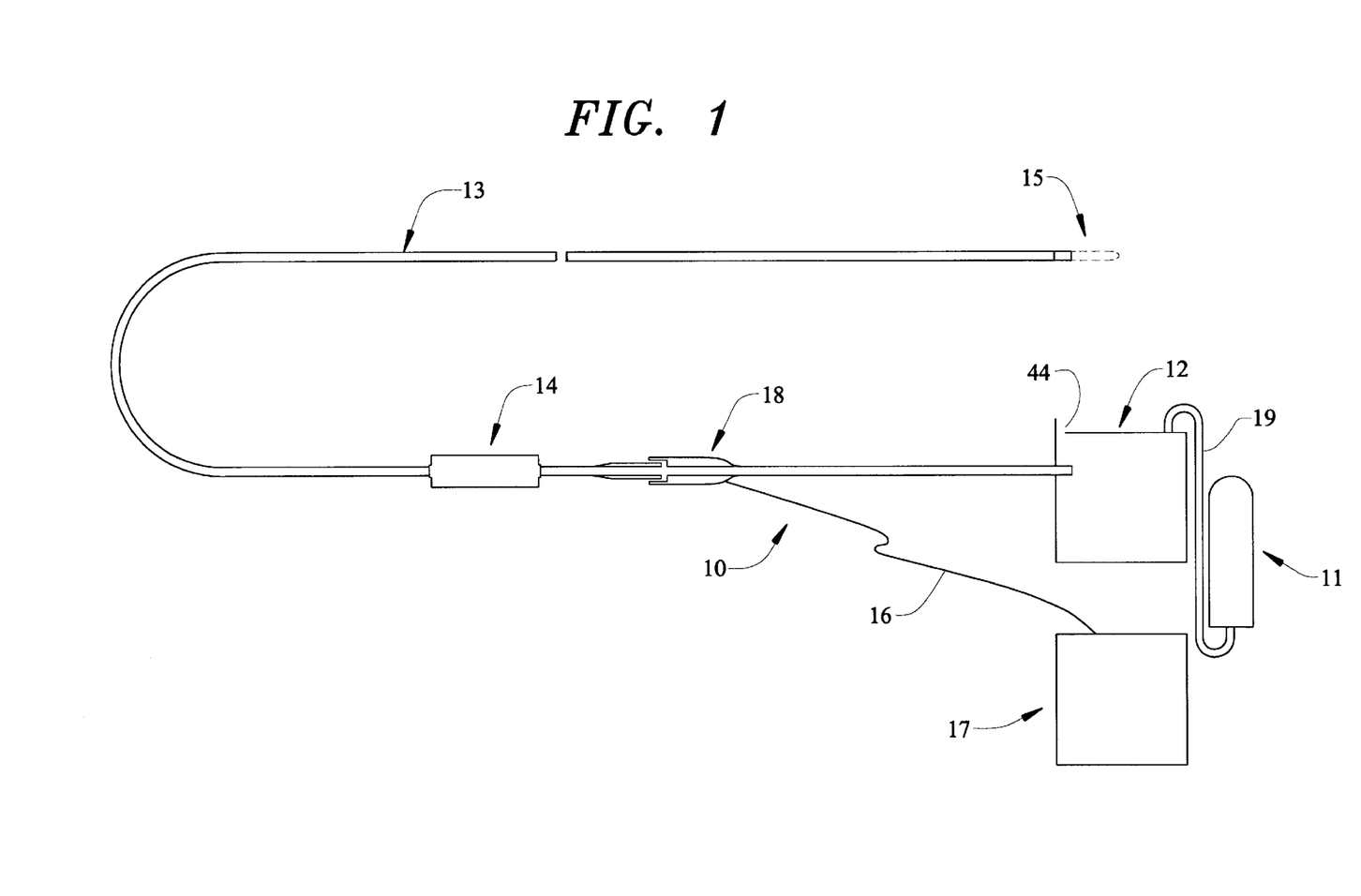
FIG. 1 is a block diagram of the elements of a cryosurgical system including the tip.
Figure 2:
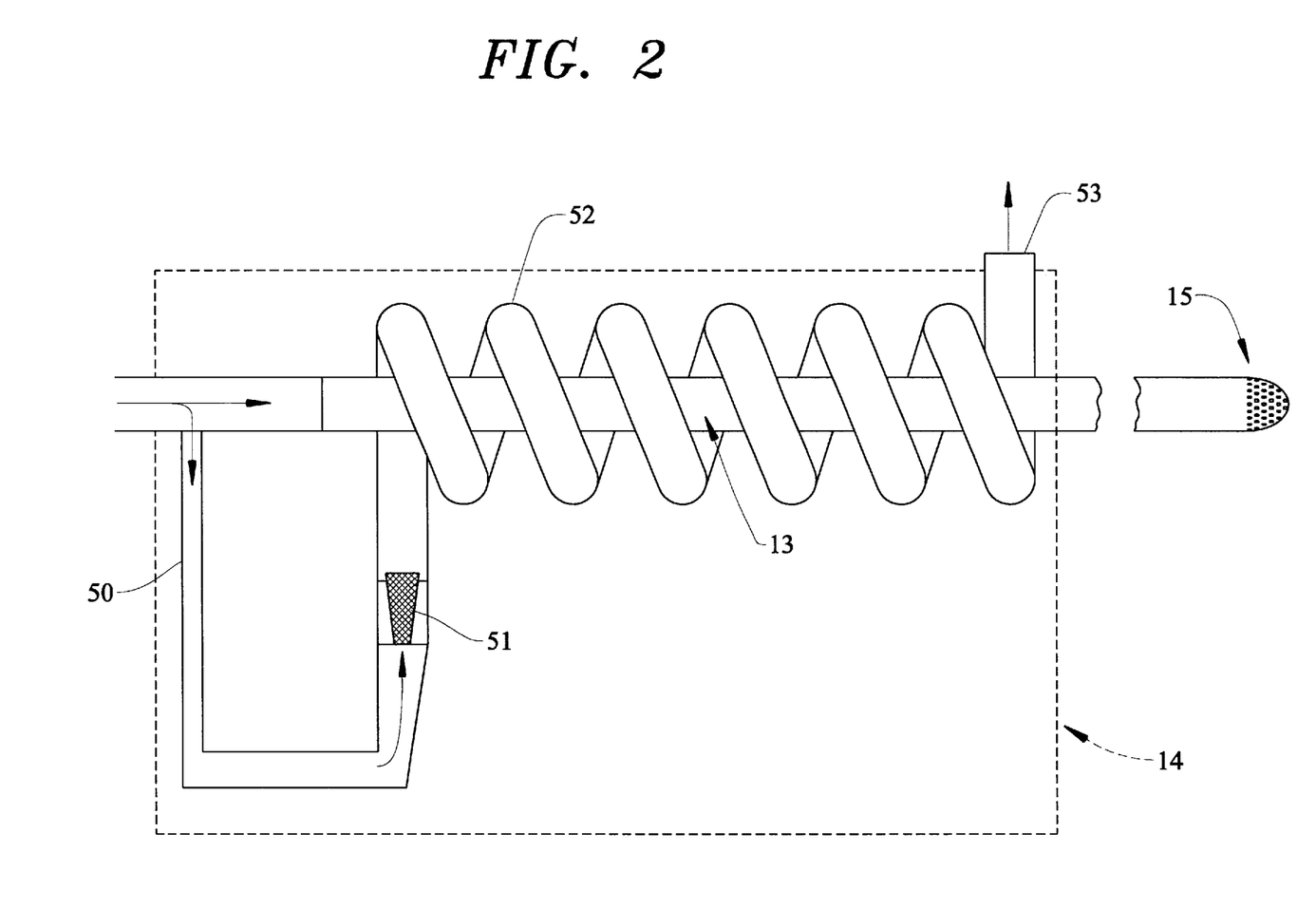
FIG. 2 is a partial schematic of the liquifier.

As shown in FIG. 1, the present invention describes a dual action cryotip system 10 which comprises a coolant source 11 connected to a console 12 and a shaft 13 permitting the operator to deliver the refrigerant in a contact or in a contact/spray tip 15 having a cooling chamber. The cooling chamber of the tip 15 can be connected to the shaft of the probe for feeding the cooling chamber with the gas and/or liquid refrigerant including at least one axial central inner bore. The shaft 13 has a liquifier 14 interposed along its length. One embodiment of the liquifier 14, shown in block diagram in FIG. 2, provides additional cooling to the shaft 13 to increase the efficacy of the tip 15. The tip 15 may have a matrix built into the cooling chamber that receives the gas-liquid refrigerant mixture, enhancing heat exchanges with the wall of the tip, lowering the gas pressure entering the cooling chamber. An electrical line 16 connects the electrically conductive outer wall of the chamber, or electrical sensors of the the chamber, to the cryosurgical imaging system (CIS)17 allowing the operator to monitor the freezing of tissues and the functioning of the probe.

The liquifier 14, as shown in FIG. 2, is disclosed in Polish Patent Application, P 314380 filed May 22, 1996. The refrigerant entering into the liquifier by shaft 13 is split into two flow paths. One flow path continues in shaft 13 to the probe tip 15. The other flow path enters line 50 and continues through the Joule/Thomson nozzle 51 into a low pressure heat exchanger coil 52. The flow through line 50 is illustrated as exiting the liquifier 14 to atmosphere at exhaust 53, in FIG. 2. However, the exhaust may be removed by line to the console 12, if desired. The coil 52 surrounds shaft 13 and further reduces the temperature in the shaft. The Joule/Thomson nozzle 51 increases the energy available at the probe tip 15 by a factor of 0.3 by converting the gaseous flow in shaft 13 to a liquid. The liquifier also allows the system to reach operating temperatures more rapidly. This embodiment is convenient for a one or two probes system, however other embodiments would be selected for a multiple probe system using more than two working probes simultaneously.

The present invention further provides different dual tip type cryosystems comprising the above described contact-spray tip, a rigid or flexible shaft connected to the tip, a handle 18 allowing manipulation of the probe shaft and/or tip, and a hose line 19 connected to the refrigerant source. In a preferred embodiment the cooling source is a $N_2O$ high pressure (700 psi, 50 bars) cylinder connected to a console 12 that controls the feeding and exhausting of the cooling medium. Moreover, the sensor(s) electrically connected to the shaft are also connected to the CIS 17.

In addition, the present invention provides electrical and or mechanical means to deliver and to occasionally exhaust the refrigerant from the cooling chamber in accordance with the image of cryosurgical effects displaying in the computer screen coming with the CIS.

The present invention still further provides methods of conducting a cryosurgical procedure on selected external or internal tissue or hollow body organs and systems, such as the pulminary, digestive, and urinary tract in the human body using a contact spray system built into a one or multiprobe device.

The present invention provides a cryosurgical system including a refrigerant source connected to a delivery tube giving access to a cooling chamber of a contact spray tip, an exhaust, made of either vent holes or of a tube concentric to the delivery tube, valves controlling the delivery and exhaust of cryogen, at a rate corresponding to the optimal freezing of tissue selected by the operator, the valves circulating cryogen according to the electrical signals processed in the CIS to optimize the flow rate.

The invention provides a contact spray system adapted to the location of the targeted tissue external or internal to the body.

The cryoprobe system may be positioned at said selected targeted tissue under direct or indirect imaging guidance and the valves activated in the first delivery tube whereby cryogen is caused to flow from said cylinder 11 said contact/spray cryoprobe 15 to generate freezing temperature therein, said freezing temperature being transferred to said tissue in two freezing steps, a preparing step of contact, closed end mode to freeze a tiny layer of tissue then an operative step of contact/spray mode wherein, upon application of said cryogen, the operation is pursued to the achievement of the selected freezing effect monitored in real time by the electrical sensors built in the probe tip and upon the attainment of the freezing effect said feeding valve is manually or automatically closed, the probe tip is actively or passively reheated, said probe tip is detached from the tissue and, if necessary, reinserted in another selected location of the tissue to complete the procedure.

Figure 3:
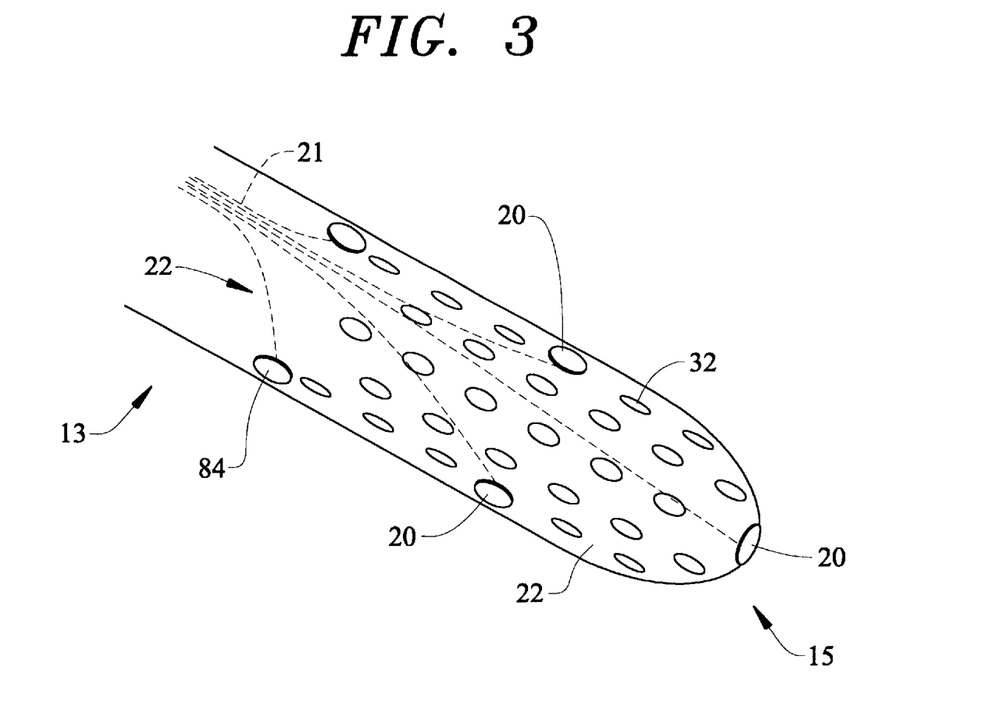
FIG. 3 is an elevation view of a tip of this invention.

As previously stated, the dual function spray/contact cryoprobe tip 15 is intended for using the efficient power of liquid refrigerant directly contacting the tissue through a tiny layer of rigid frozen tissue. Also the probe in whole or in part is used as a sensor of bioelectrical impedance, temperature, light and the like, to monitor the ice ball extension around it or to monitor the probe function. A convenient electrical connection to the CIS is set between the electrically conductive sensor and the processing unit. The probe tips 15 can be constructed to bear a multiplicity of bioelectrical impedance sensors 20, as shown in FIG. 3, suitably insulated from each other to permit a more selective monitoring of the ice ball when required, for example monitoring irregularly shaped ice balls. The tip 15 may also include a reference electrode which completes the electrical circuit in the body when placed in contact with the tissue.

Figure 10:
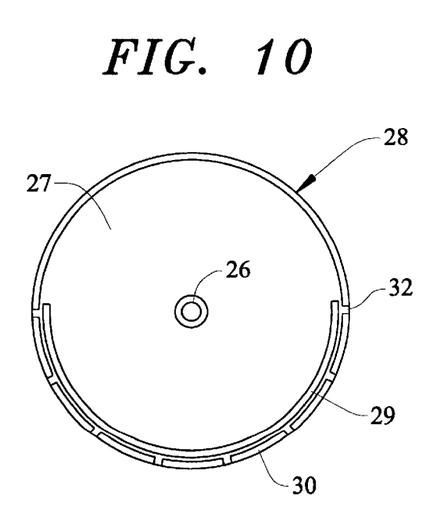
FIG. 10 is a cross section of another probe tip of the invention.
Figure 11:
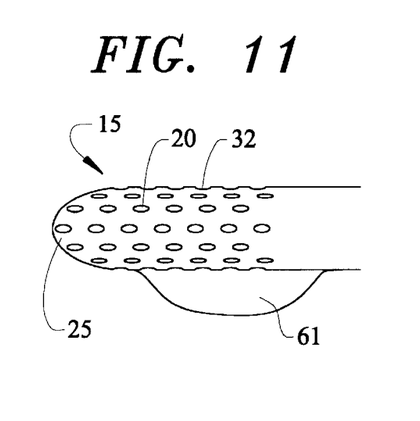
FIG. 11 is a plan view of another probe tip of this invention.

When using a single probe and electrode, certain assumptions are made concerning the resultant ice ball. The ice ball is considered as developing uniformly and symmetrically about the probe and that the volume of change-of-phase extends outwardly from the center in a homogeneous manner. However, there are operative situations where the ice ball does not develop symmetrically or homogeneously around the surface contact area. This occurs when the pressure of contact is not equal in every zone contacting the tissue thus changing the heat exchanges between probe and tissue. It can also result from the consistency of the tissue itself, e.g. the presence of normal soft tissue and scar tissue in the same area or there is a significant heat sink, such as a large blood vessel or other structure, in the region of the ice ball. Also, the probe tip may be designed to shape the ice ball in a particular direction, as shown in FIGS. 10–12.

Figure 4:
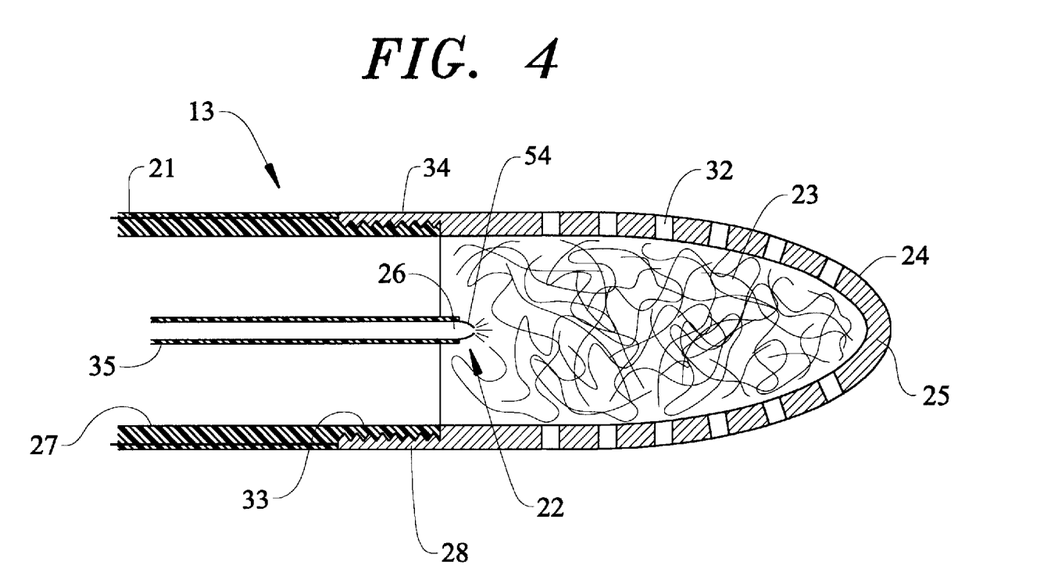
FIG. 4 is a cross section of an electrically conductive tip of this invention containing a matrix.

In this embodiment each sensor is connected via a dedicated electric wire 21 connected by line 16 to the processing unit. Other sensors, such as thermocouples, can also be incorporated, coupled to or independent of the impedance sensors (electrodes). The probe tip 15, shown in FIGS. 3 and 4, is made of a cooling chamber 22 and of a matrix 23 centered into the chamber and in contact with the inner wall of the chamber and with the delivery tube. The probe tip may be provided in several different lengths, diameters and shapes. It includes an outer hollow shell 24 with a narrow and usually blunt end 25, and an open end. The outer hollow shell will be preferably made of stainless steel or copper or of any material known as being good thermal and electrical conductors whenever the probe tip is used as a unique tissue sensor. Fitting within the shell, is an internal refrigerant delivery tube 26, a refrigerant return vent or exhaust tube 27, and a connecting member 28 for joining the shaft and the freezing zone at the blunt end. The shaft includes an electrically and thermally insulated region at the open end. One embodiment, shown in FIG. 3, of the probe tip has a single walled tube, wherein the wall is a simple layer made of porous material (organic, pure metal or alloy, composite plastic). The tip 15 has multiple sensors 20 and a reference electrode 84 to complete the circuit. The reference electrode 84 is placed in contact with the surface of the tissue. The single wall tube may have holes 32 or a grid of selected size attached. In this single wall version the porous material can also be the matrix itself.

Other embodiments, shown in FIGS. 7–10 and 12, have a double wall 28 wherein the wall is made of two concentric layers of the tip creating two superimposed cooling chambers. The inner one 29 and the external one 30 simply rotating or slipping over each other on command. Such rotation or displacement permits the two sets of apertures 31 and 32 of each chamber to match for acting on spray position, and to close the cooling chamber in the other position. In the closed position, the tip provides light cooling of the target tissue immediately preceding spray cooling. Other embodiments of this tip permit shaping of the ice ball in a selected direction by selective opening of apertures in a portion of the circumference of the tip or using tips with apertures only in selected portions of the circumference or both.

Figure 12:
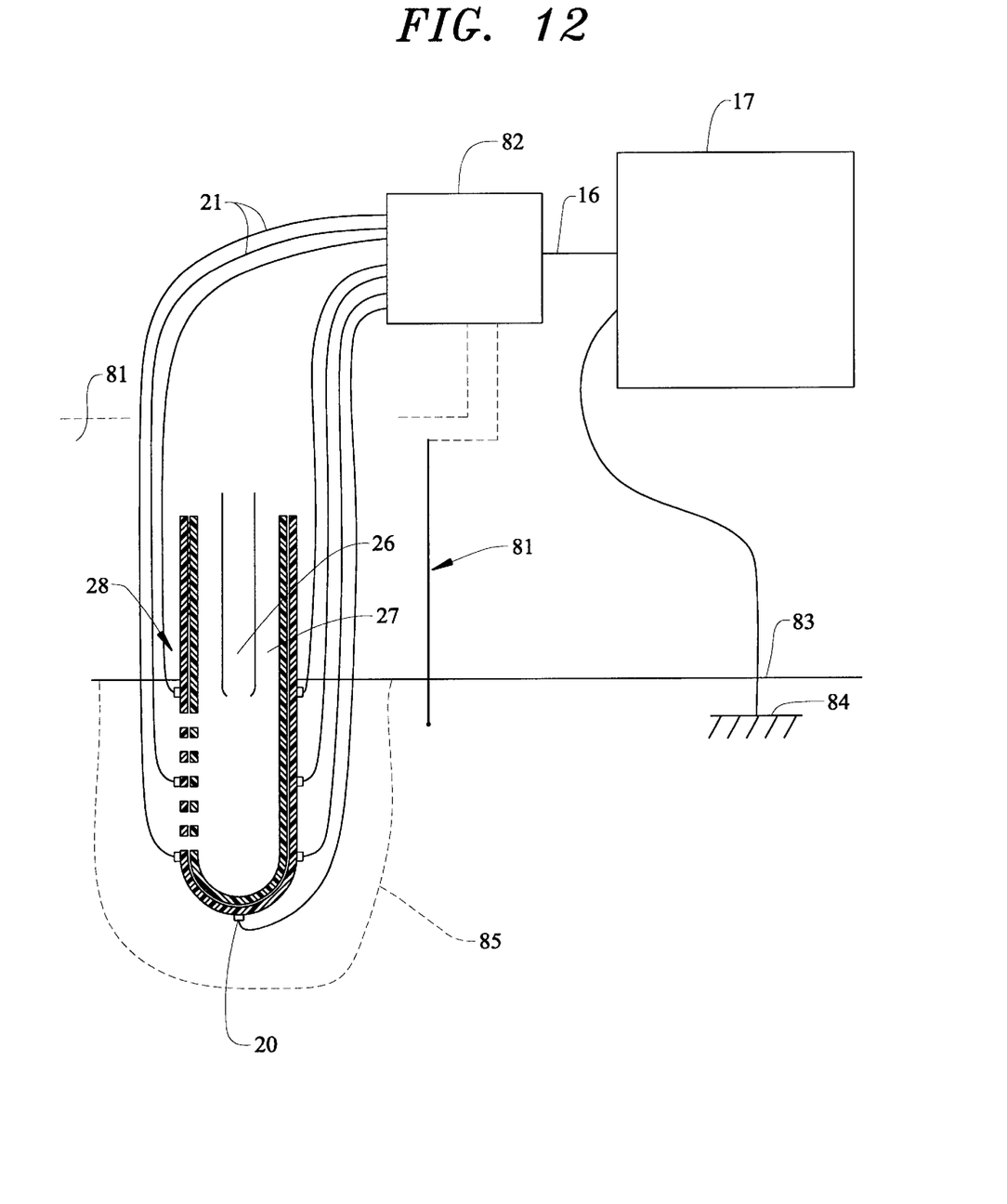
FIG. 12 is a schematic of a modified probe tip of this invention illustrating multiple sensors.

In FIG. 12, an operative disposition of a double walled tip 28 is illustrated including multiple sensors 20 and multiple tissue sensors 81, such as thermocouples or impedance needles. In FIG. 12, the necessary wiring is illustrated external to the probe tip 15 and probe shaft 13 for clarity but would normally be contained within the tip and shaft or within the walls of the tip and shaft. These sensors are connected to a CIS for real time imaging of change-of-phase in the tissue 83 as the ice ball 85 expands. Interposed between the sensors and the CIS is a dispatcher/scanner 82 which collects readings from the different sensors and feeds the CIS. A remote electrode 84 is attached to the body to complete the circuit. As stated above, the electrode 84 may be incorporated into the probe tip to contact the surface of the tissue. In this embodiment, the ice ball is shaped by the open apertures on one portion of the tip vectoring refrigerant in one predominant direction.

The probe tip 15 of FIG. 11 has an array of apertures 32 disposed on part of the circumference of the probe tip. Diametrically opposed to the apertures, the tip carries a balloon 61 which may be selectively inflated and deflated. The balloon 61 provides thermal insulation to the tissue adjacent to the inflated balloon and applies vectored pressure to the probe to force the apertured portion of the tip into more intimate contact with tissue in the direction of the desired formation of the ice ball.

In the usual embodiment with a refrigerant return, the delivery and the refrigerant return tubes 26 and 27 are arranged in parallel and most preferably are in the form of concentric tubes having the same longitudinal axis as the hollow shell. Also the inner delivery tube reaches the region of the matrix 23 located into the boiling chamber and its length is usually superior to the return tube, when present.

Figure 5:
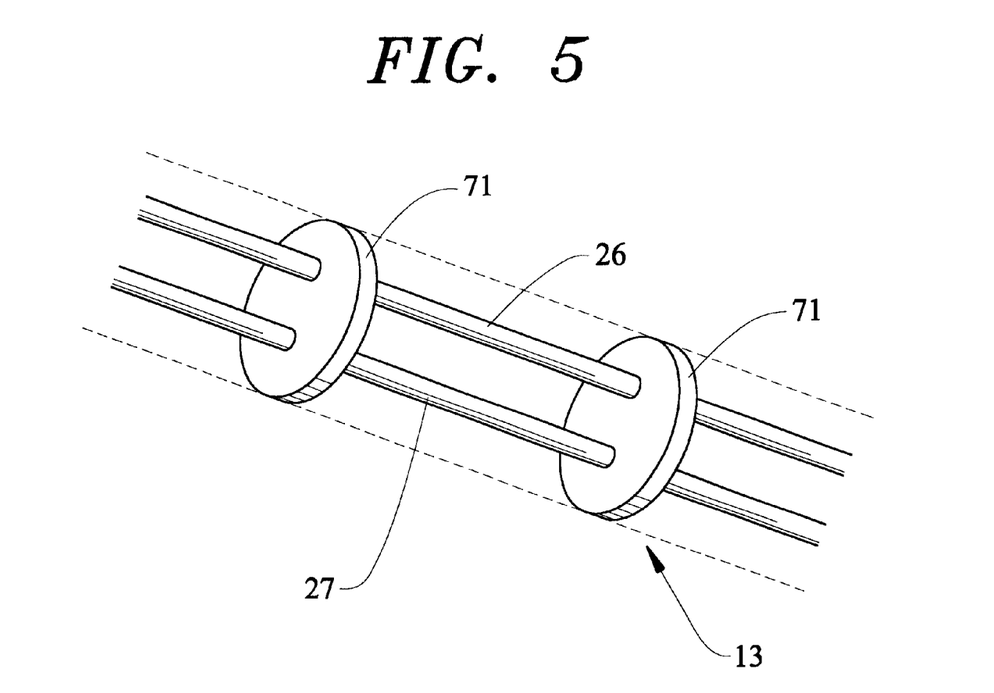
FIG. 5 is a partial cut away of a modification of the shaft of the invention.
Figure 6:
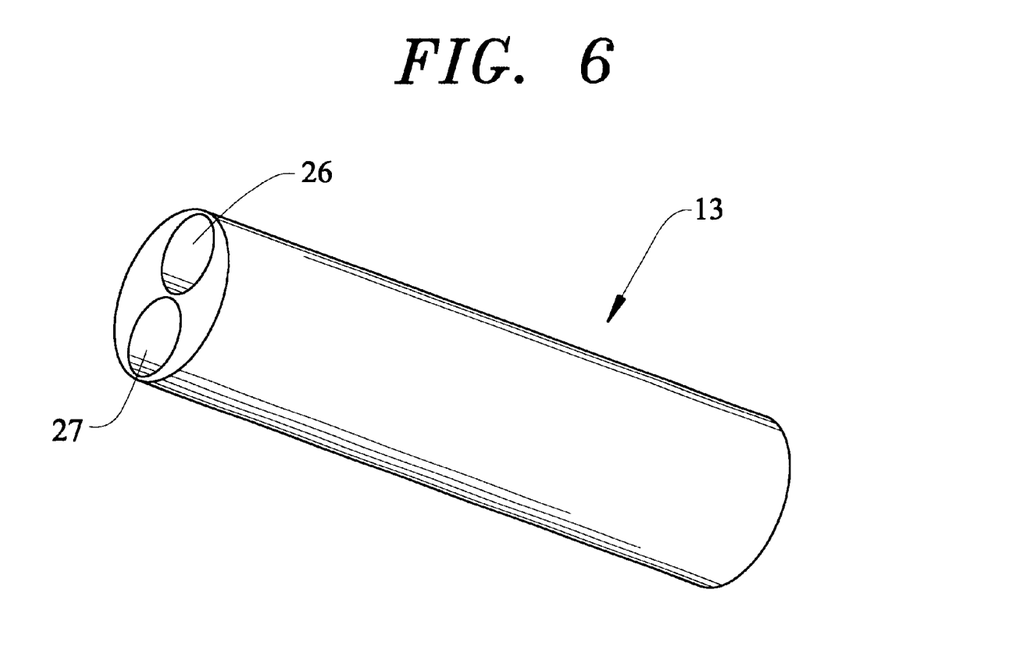
FIG. 6 is a plan view of another modification of the shaft of the invention.
Figure 7:
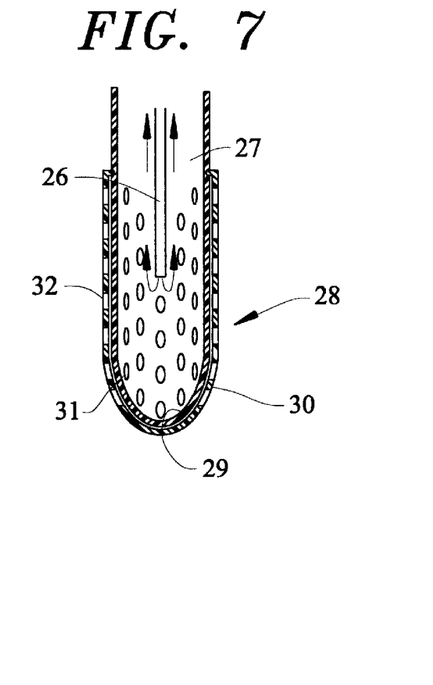
FIG. 7 is a cross section of a probe of the invention with relatively movable double walls.
Figure 8:
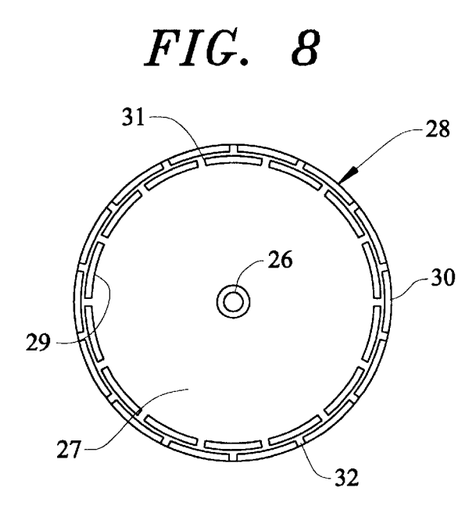
FIG. 8 is a cross section of a probe tip of FIG. 7 in the closed position.
Figure 9:
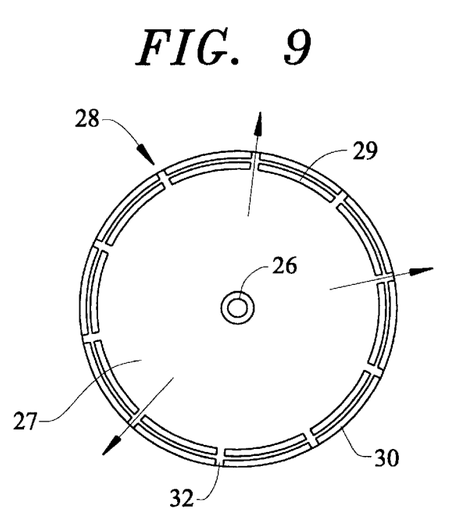
FIG. 9 is a cross section of the probe tip of FIG. 7 in the open position.

Another embodiment, shown in FIG. 6, consists of a single double lumen tube wherein a common wall divides a tube into a two passageways for the refrigerant supply 26 and refrigerant exhaust 27. Alternatively, as shown in FIG. 5 separate tubes 26 and 27, arranged in parallel may also be used for the same purpose of feeding and exhausting the refrigerant. Depending to the refrigerant used, spacer discs 71 (i.e. made of Teflon) can be provided that separate the feeding and exhausting lines for avoiding undesired freezing of the pipe.

It is contemplated that the cooling systems most used in such a tip would be the introduction of low boiling point refrigerant like $LN_2$, gas expansion utilizing a Joule-Thomson effect with such gas as Nitrous Oxide or Carbon Dioxide, latent heat of vaporization such as with Freon, or precooled gas and liquids. It is obvious that one can use any other cooling medium that can possibly be used in a more effective manner in direct contact with the tissue, depending on the nature and volume of the tissue.

In the simplest embodiment, the inner delivery tube 26 is made of rigid or flexible metal (stainless steel or alloy of copper/nickel, etc.) or plastic, or composite (coated plastic, braided plastic for reinforcement and resistance to high pressure and/or for electrical conductivity) and is simply concentric to an external wire tube coated with an electrically insulating layer. A mechanical connection links the tip at its open end to the shaft 13 either in a permanent manner or using threads on the external open end of the tip that permit screw tightening or adhering with an adhesive onto the metallic or plastic part of the shaft. In another embodiment the tips are interchangeable and the shaft is equipped with threads 33 that cooperate with threads 34 on the open end of the tip. One can interchange the tip by simply screwing the selected tip onto the shaft.

Given that the applications of cryosurgery are now spreading to deep body organs and lesions in the body, the probe tip and shaft dimensions and structure must permit insertion of the said tip at the desired location. This is usually done through natural, and artificial openings, e.g. a minimal puncture site or surgical incision, and/or endoscopes in areas where gas bubbles coming from vaporization of the liquid or liquid/gas mixture couldn't harm the body. Hollow body structures like the digestive, pulmonary, or urinary systems are well suited for this method. Body organs can also be targeted as described below. The probe shaft may be rigid or flexible according to the intended use: direct application through a natural or artificial opening (i.e. rectum, vagina, mouth, etc.) or through the operative channel of endoscopes, or through a guiding catheter. In a preferred embodiment, this cryosurgical device is adapted to be slidably inserted through a catheter or an endoscope to conduct cryogenic refrigerant from a high-pressure supply to target tissue disposed beyond its distal end. To that end and so as to be suitable for a variety of catheter or endoscopic applications, particularly in the hollow body organs, the cryoprobe instrument provided in accordance with an embodiment of the present invention has a length of at least 90 cm and more preferably on the order of at least 1.5 m. While suitable lengths will depend on the instrument with which the cryoprobe is to be used, it is not expected that a length of greater than about 3 meters will be necessary.

Figure 13:
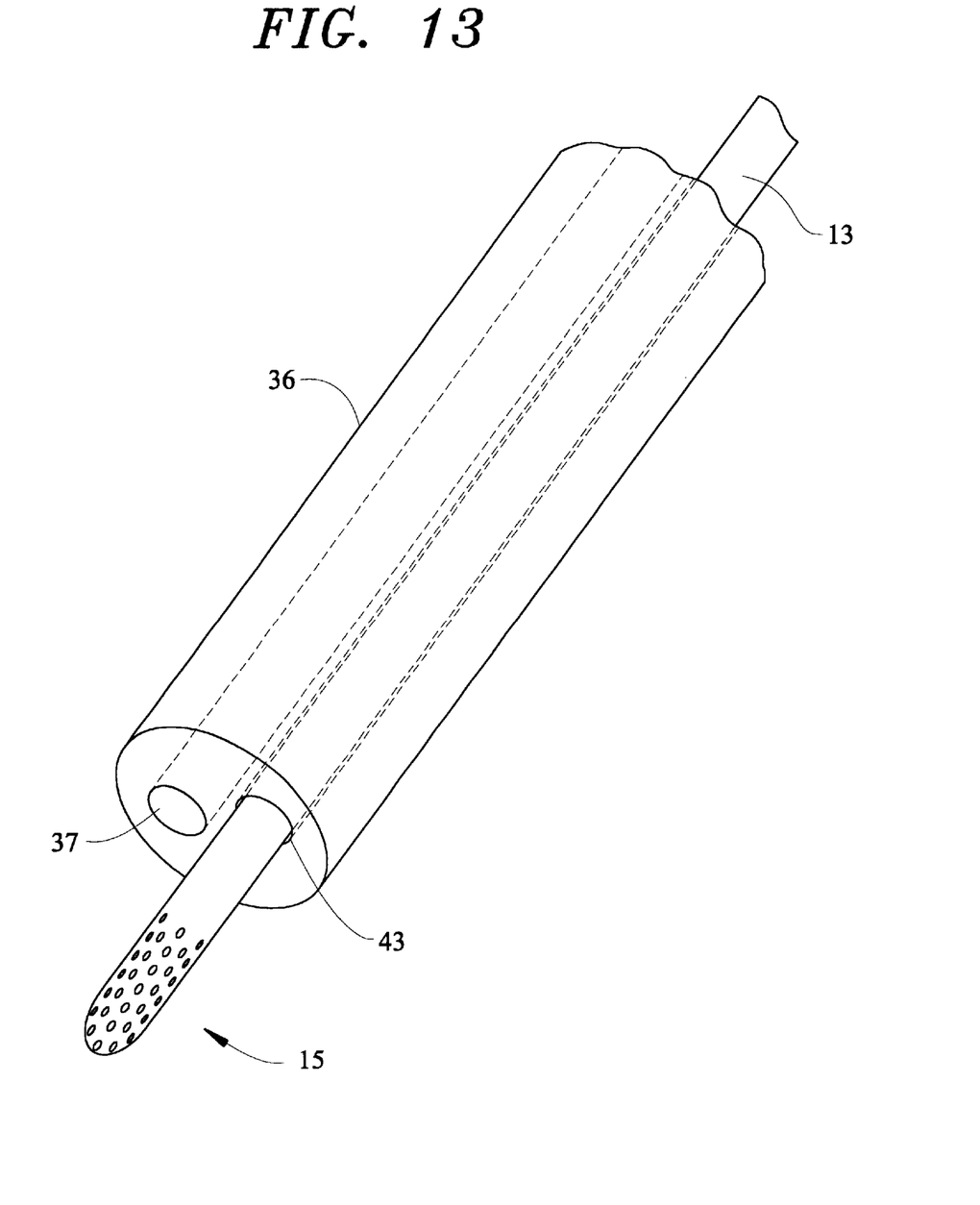
FIG. 13 is a partial plan view and cut away of the probe and a endoscope.

To withstand the pressure of the cryogenic refrigerant and to provide the requisite flexibility, in spite of temperature fluctuations the shaft 13 has inner lumen portion of the cryoprobe including an elongated tube 26, preferably formed from stainless steel or from an alloy of copper and nickel. It can also be made of braided material, such as polyamide, polyimide or the like. Inner tube 26 has a Joule/Thomson nozzle 54 near the end so that the portion of the probe 23 extending beyond the nozzle may be flexible to permit bending and steering of the probe. Outer tube 27, in FIG. 13, provides a lubricious surface, to facilitate feed through the operative channel of an endoscope or through the lumen of a catheter. This surface adds a measure of electrical and thermal insulation, minimizes loss of cooling effect; and protects the inner feeding tube from excess binding or kinking. The tube 27 is a thin plastic (made of polymers such as polyamide, polyimide, Teflon, and the like) or metal spiraled (stainless steel)—plastic coated tube in concentric relation to the inner tube.

In an exemplary and preferred embodiment, the thin outer layer 35 or tube is provided by a thin walled polytetrafluoroethylene (Teflon) tube disposed in concentric relation to the inner feeding tube. Other materials than Teflon can also be used like, polyethylene, polypropylene, polyimide and the like.

In order that the cryoprobe may be fed through a catheter or an endoscope 36 to a target site, the outer diameter of the shaft must not be greater than the passage defined through the lumen of the catheter 36 or the lumen of the operative channel of the endoscope. Thus the outer diameter of the shaft of the cryoprobe should preferably be about 5 mm or less and more typically between about 1.8 mm and 3.30 mm. Further, the inner tube must have a suitable portion having an inner diameter of about 0.9 mm, where the cryogen pressure is between 450 psi and a maximum of 700 psi. an inner diameter in the recited range provides for a steady flow of cryogenic refrigerant from supplying source to tip. Also in this very small diameters allows the operator to feed the inner tube with the cryogen in the liquid phase at or near room temperature and at higher pressure, thus avoiding the risk of gas expansion along the tube and inherent drawbacks. It is well known that if the inner diameter of the feeding tube is too small, then depending upon the cryogen, the source pressure, and the like, the resulting flow restriction may entail an undesirable cooling along the tube length. The upper limit depends upon the operative lumen or channel diameter, and the combined thickness of the inner tube and the outer returning tube and/or protective tubing, coating, as well as the desirability of avoiding undue cryogen expansion before the cryogen exits the nozzle. In an exemplary embodiment, the inner tube has an outside diameter of about 1.2 to 1.4 mm, and a wall thickness of about 0.150 mm. Further in an exemplary embodiment the outer diameter of the outer tubing, Teflon tube or metallo-plastic tube, is between 1.8 mm and 3.30 mm with a wall thickness of about 0.9 mm to 1.0 mm. Also this feature allows designing very long probe shafts.

As is apparent from the foregoing, the outer and inner diameters of the inner tube and the outer layer or tube will depend upon the flow passage diameter deemed appropriate, the wall thickness of the tubes, including a gap between the tubes if necessary or desirable for the return exhaust tube, and the diameter of the operative channel of the selected positioning instrument.

As liquid refrigerant tends to run, in the form of droplets, onto undesired areas, particularly when the surface of tissue is frozen, as with the use of $LN_2$, a perfect monitoring over the cryogenic liquid feeding to the boiling chamber is required to avoid a possible reservoir effect. This effect is due to the accumulated liquid in the matrix that continues to vaporize even after closure of the feeding valve. To that effect feeding of the chamber is regulated by a continuous monitoring of the ice ball growth around the probe as by complex impedance measurements and by simultaneous measurements of the exhausted refrigerant at the impedance and/or temperature sensor(s) 20 located at the junction between the shaft and the tip. A complete boiling/vaporizing of the liquid refrigerant is monitored by the temperature and impedance sensors located at the junction connection between the probe and the shaft, thus optimizing the probe function and avoiding retro freezing of the shaft that could be potentially harmful for the endoscope or the body.

The heat exchanging matrix 23 is disposed within the boiling or expansion chamber of the tip (depending on the selected refrigerant) for interaction with cooling fluids flowing therethrough for enhancing heat transfer within the expansion chamber and for providing a complex and random cooling fluid flow path through the expansion chamber. Also it lowers the pressure of the liquid entering the cooling chamber, so that there is no spray of liquid through the external outer openings of the cooling chamber. This system of matrix forces the liquid to flow out the chamber openings in the form of droplets. The matrix fully or partially fills the expansion chamber. The matrix 23 is usually made of material indicated for a heat exchanger suitable for a selected refrigerant, such as, copper, or silver, or Teflon, nylon, or other suitable materials. The matrix may be in the form of filaments, porous structure, or microspheres. When the matrix is made of electroconductive material, like metal, metallic alloy or composite braided plastic, it can also serve as a means of contact between the electroconductive probe tip and the electroconductive inner tube. This embodiment is used when the outer tubing of the shaft 13 is made of electrically insulating material.

Such a contact/spray tip can include any other ablative function required for action on tissues, like heating through electro surgery, or laser irradiation through the adjunction of a lumen able to conduct the beam in a region adjacent to the probe tip.

Depending on the intended application, an instant rewarming of the tip may not be necessary or desirable. It can be done if necessary by flowing a hot gas at low pressure into the expansion chamber.

There are various methods of application the spray/contact probe to a selected tissue or target, for example, interstitial freezing or superficial freezing.

For the application of interstitial freezing the cryoprobe tip is inserted into the tissue at the desired depth selected by the operator and sufficient to permit the destructive ice ball to entail the margins of the target. There are a two probes technique and the single probe technique.

In the two probes technique, the operator first uses a closed tip probe inserted into the target tissue at the desired depth, then cooled for a time sufficient to freeze a few millimeters of tissue around the probe. This preparation of tissue hardens it and after instant reheating and removing of this first probe, the second operative spray probe is inserted into the frozen duct for completing the freezing process in the manner decided by the operator, under a selected monitoring technique, for example, ultrasound or magnetic resonance.

In the one probe technique, the same probe fulfills the two requirements of hardening a thin layer of the tissue then treating it without moving the tip from its position. An embodiment of this technique consists in introducing a catheter 36, shown in FIG. 13, at the desired location through direct or imaging guidance, inserting the probe tip 15 into the catheter, introducing refrigerant into the probe while it remains with in the bore of the catheter to initially freeze the tissue while the catheter wall prevents the liquid/gas mixture from escaping. The catheter is then withdrawn, as in FIG. 13, a few millimeters or centimeters to let the gas/liquid mixture flow freely in contact with the tissue. The catheter inner diameter and the material are calculated to adapt to the tip size and to be moved smoothly when it is deemed necessary for the probe application. This technique allows shaping of the ice ball according to the numbers and location of openings exposed by the controlled withdrawal of external catheter.

The cryoprobe tip may be designed to provide a particular shaped ice ball, in operation, given that the ice ball develops in the direction of the maximal heat extraction. Such designs include selectively opening and closing certain apertures, either radially or longitudinally, in the tip to dictate the shape of the ice ball, shown in FIGS. 10, 11 and 12. Also, certain segments of the tip may be thermally insulated. In such probe tips, the electrical sensors are located to effectively monitor the correspondingly shaped ice ball.

Another technique of using a single probe requires that the probe tip be completely embedded in the tissue, while the operator is charging the inner tube with the gas refrigerant at a low rate and/or at a low pressure, depending on the refrigerant that is used so as to permit the ice ball to form by the action of gas/liquid refrigerant at the interface of the probe and tissue. The expanded gas resulting from expansion of liquid flows into the cooling chamber and is taken off in the concentric return tube. The return tube is connected to the handle 18 and hose line back to the exhaust opening 44 located at the rear board of the console. In very small sized probe, 2 mm and under, an active suction system permits withdrawal of the returning gas. The freezing process is monitored by electrical sensor(s)20 located at the outer wall of the tip in contact with the tissue. Other electrical sensor(s)20 can be located at the junction of the shaft and the probe so as to monitor an occasional undesired freezing of this zone requiring interruption of freezing. Other types of sensors, such as thermocouples, may be used in place of, or coupled with the electrical sensors. The same sensors, when it is deemed desirable to the operator, are inserted into the target tissue itself.

In another technique, the probe tip is inserted into the tissue so as to preserve a segment outside the tissue that permits the gas to escape the cooling chamber and to lower the risk of inflating the tissue. The gas exhausted at or near the junction between the shaft and the tip, by vent holes, is released into the atmosphere of the operative area and withdrawn form the area by an active aspiration, as by bore 36 shown in FIG. 13, of the operative endoscope suction means. Such a construction is preferred for very small probes (under 2 mm outer diameter) used for applications in to hollow body organs (pulmonary, urinary, or digestive tract) through the operative channel of small sized endoscopes.

In yet another technique, the probe tip 28 is made of two concentric hollowed expansion chambers 29 and 30 that can rotate upon each other to match the apertures 31 and 32 on command. In the closed tip position of FIG. 8 the probe is inserted into the tissue then activated to get the hardening, then a commanded rotation of the probe tip superposes the apertures permitting the liquid/gas mixture to flow onto the tissue. An embodiment of this dual action tip is a quarter circle rotation of the inner chamber 29 commanded while the external chamber 30 adheres to the tissue resulting in the matching of the holes of the concentric chambers. Any other variation of tip construction, such as longitudinal sliding of a solid inner tube within an apertured outer tip to expose apertures in the outer tip, to allow direct contact of the refrigerant and tissue is within the scope of this invention.

Figure 14:
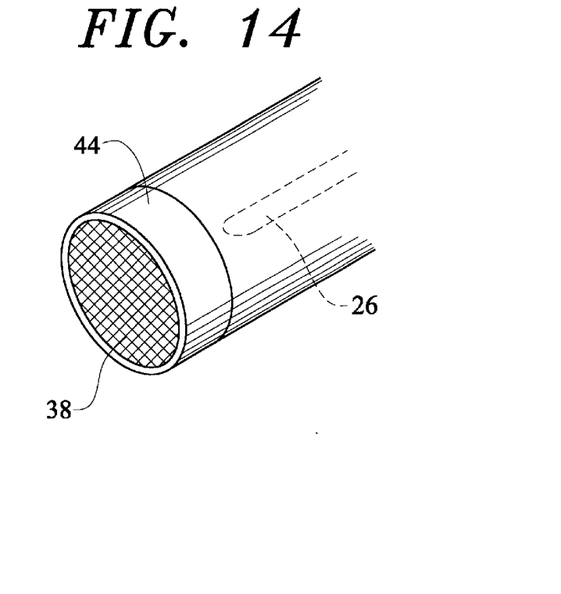
FIG. 14 is a plan view of another modification of the probe.
Figures 15, 16:
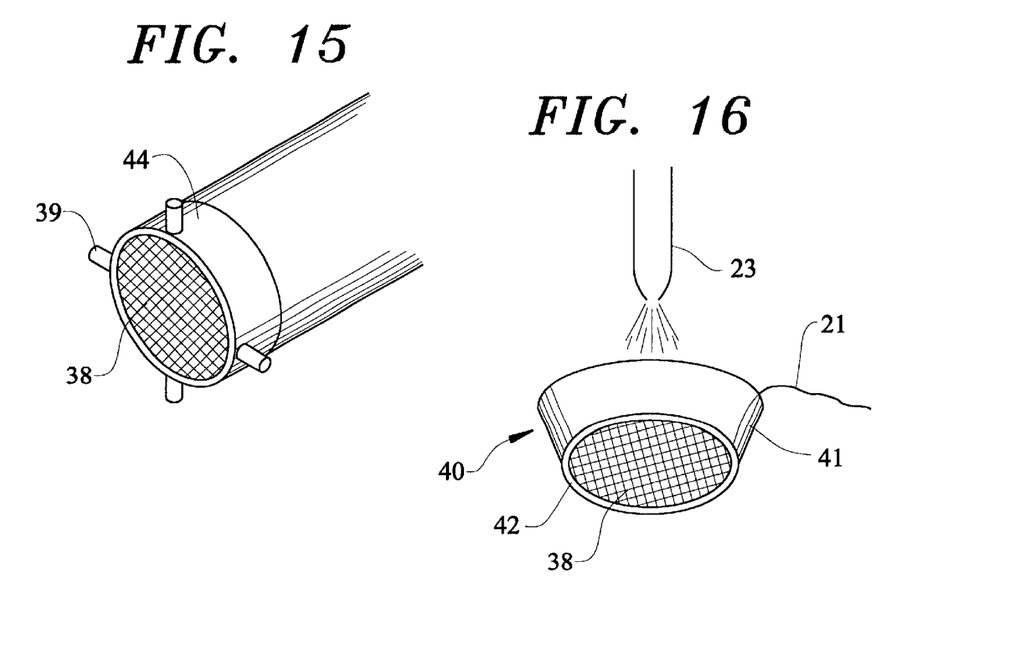
FIG. 15 is a plan view of another modification of the probe.
FIG. 16 is a plan view of another modification of the probe.

For the application of superficial freezing, there are various embodiments. In the first one, the end of the tip in contact with the tissue is either a tube with a through bore or with a grid 38 extending across the end of the through bore, as shown in FIG. 14. In the hollowed shape, the contact interface between probe and tissue is the periphery of the tube 44 which may be cylindrical. This contact surface can be expanded as required for the purpose of electrical measurements by additional retractable sensors 39 made of electrically conductive material and attached to the tip 15 as shown in FIG. 15. In the rest position, the sensors 39 are retracted so as to facilitate positioning of the probe and then they are deployed in the operative conditions to contact the tissue. The presence of the grid 38 is for the same purpose of increasing the surface of sensor contacting the tissue to improve electrical measurements.

In another embodiment, shown in FIG. 16, the tip, also used as the sensor, is shaped so as to concentrate the spray as in a cone. The tip 40 is made of plastic material 41 such as Teflon or other composite plastic. The conductive material in contact with the tissue allows recording electrical measurements. The hollowed metallic ring 42 and/or grid 38 contacting the tissue may be connected to the CIS. The ice ball growth formed under and around the cone is monitored by the CIS.

A typical surface application is when only a fast superficial freezing is desired on a large surface. In dermatology, the process of cryodermabrasion is a perfect example. There is a need to freeze a large surface of the superficial layer of the skin of the face. But it is difficult to monitor the destructive/abrasive process so that the procedure is very operator dependant. A means to get a better real time prediction of depth of cryodestruction is with the spray oriented into the sensor simply put on the skin surface. The material used for the sensor must also be a good thermal and electrical conductor, such as, copper, silver, or composite. It is also shapeable for the purpose of close adaptation to the surface irregularities.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

I claim:

1. A dual action ablation probe for necrosis of tissue by spray and contact comprising a tubular shaft for delivery of a cryogen, said shaft having a first end and a second end, an elongated hollow tip having a proximal end and a distal end and an interior space surrounded by a continuous sidewall, said proximal end of said tip connected to said first end of said tubular shaft, and said tip including at least one aperture whereby said cryogen lowers the temperature of said tip to ablate tissue by contact and said cryogen passing through said at least one aperture ablates tissue directly by spray.

2. A dual action ablation probe of claim 1 wherein a matrix is disposed in said hollow tip and contacts said sidewall, said matrix enhancing the heat exchange between the cryogen and said sidewall and providing a complex flow path within said tip.

3. A dual action ablation probe of claim 2 wherein said matrix is any one of the group of materials consisting of filaments, porous three dimensional structure, or microspheres.

4. A dual action ablation probe of claim 1 wherein said shaft has a liquifier means disposed on said shaft between said first and second ends for reducing the temperature in said shaft.

5. A dual action ablation probe of claim 1 wherein said distal end of said tip has a plurality of apertures in a portion of said distal end for direct contact of the cryogen.

6. A dual action ablation probe of claim 5 wherein an inflatable and deflatable balloon is connected to said distal end of said tip opposite said apertures.

7. A dual action ablation probe of claim 1 wherein said tip has an inner smaller hollow dome-shape cooling chamber, said tip and said chamber rotatably mounted with respect to each other, and said at least one aperture through said hollow dome-shape chamber, whereby said at least one aperture in said tip may be opened and closed by rotation of said cooling chamber.

8. A dual action ablation probe of claim 7 wherein said cooling chamber has a plurality of apertures therethrough whereby a plurality of said apertures in said tip may be opened and closed by rotation of said cooling chamber.

9. A dual action ablation probe for necrosis of tissue comprising a tubular shaft for delivery of a cryogen, said shaft having a first end and a second end, an elongated hollow tip having a proximal end and a distal end and an interior space surrounded by a continuous sidewall, said proximal end of said tip connected to said first end of said tubular shaft, and said tip including at least one aperture wherein said shaft comprises at least two lumen, one lumen for cryogen supply to said tip and another lumen for cryogen exhaust from said tip.

10. A dual action ablation probe of claim 9 wherein said elongated hollow tip is formed with a Joule/Thomson heat exchange chamber therein.

11. A dual action ablation probe of claim 10 wherein said Joule/Thomson heat exchange chamber contains a matrix.

12. A dual action ablation probe of claim 10 wherein said shaft has a liquifier disposed on said shaft between said ends for additional cooling of said shaft.

13. A dual action ablation probe of claim 1 wherein said elongated hollow tip includes at least one electrode for applying an electrical current across said tissue.

14. A dual action ablation probe of claim 13 wherein said at least one aperture in said elongated hollow tip has a grid extending across said aperture, said grid forming a sensor means for monitoring the changes in said tissue.

15. A dual action ablation probe of claim 13 wherein a plurality of sensor means are mounted on said elongated hollow tip and exposed to said tissue for monitoring electrical changes in said tissue.

16. A dual action ablation probe of claim 15 wherein said distal end includes a closed done-shape area, said continuous sidewall and said dome-shape area having a plurality of apertures.

17. A dual action ablation probe of claim 16 wherein a matrix is disposed in and contacts said distal end, said matrix being one of the group consisting of filaments, three dimensional porous material, or microspheres.

18. A dual action ablation probe of claim 17 wherein said shaft has at least two lumen, one lumen for cryogen supply and one lumen for cryogen exhaust, said distal end forming a Joule/Thomson cooling chamber.

19. A dual action ablation probe of claim 13 wherein said elongated hollow probe contains a reference electrode for completing an electrical circuit through said tissue.

20. A cryosurgical system for necrosis of tissue by hypothermia comprising at least one cryoprobe, said cryoprobe having a tubular shaft with a first end and a second end, said second end of said shaft connected to a console, said console containing valves for controlling flow of cryogenic fluid, a source of electrical power and electrical instruments for monitoring necrosis, said console adapted for connection to said source of cryogenic fluid through said valves, said first end of said shaft connected to the proximal end of a hollow elongated tip, wherein said shaft has a supply lumen and an exhaust lumen, the distal end of said tip having at least one exposed electrode for conducting an electric current, said tip having a plurality of exposed electrical sensors for monitoring electrical changes, said electrode and said sensors electrically connected to said console.

21. A cryosurgical system of claim 20 wherein said supply and said exhaust lumen are concentric.

22. A cryosurgical system of claim 20 wherein said distal end of said cryoprobe has a hollow dome-shape with at least one aperture, said hollow dome-shape forming a Joule/Thomson cooling chamber.

23. A cryosurgical system of claim 22 wherein said distal end of said tip contains a matrix.

24. A cryosurgical system of claim 20 wherein a liquifier means for reducing shaft temperature is located on said shaft between said first and second ends, said liquifier means adapted to be connected to a source of cryogenic fluid.

25. A cryosurgical system of claim 20 wherein said electrical sensors have pre-set conditions and said sensors are electrically connected in said console to a control means for actuating said valves to open and close whereby when said pre-set conditions are met said valves are automatically actuated.

26. A dual action ablation method of necrosis of tissue by freezing comprising the steps of (A) providing an elongated tubular cryoprobe operatively connected at the proximal end to a source of cryogen, the distal end of said cryoprobe forming a cooling chamber, said cooling chamber having at least one aperture therethrough, (B) operatively placing said cryoprobe in tissue, (C) as a first action initiating flow of said cryogen to said cryoprobe to reduce the temperature of said cryoprobe and freeze a thin layer of tissue in contact with said cryoprobe, (D) as a second action continuing flow of said cryogen through said aperture as a spray onto said frozen tissue, (E) ceasing cryogen flow, (F) heating said cryoprobe and removing said cryoprobe from said tissue.

27. A dual action ablation method of claim 26 wherein said cooling chamber of said cryoprobe includes an inner and outer walls, each with a plurality of apertures, said inner and outer walls being relatively movable in regard to each other, said relative movement bringing said plurality of apertures into and out of registry with each other, including the steps of (A) relatively moving said inner and outer wall so that said plurality of apertures is out of registry, (B) inserting said cryoprobe in tissue, (C) initiating flow of said cryogen to freeze a thin layer of said tissue by contact with said cryoprobe, (D) relatively moving said inner and outer wall to bring said plurality of apertures into registry, and (E) continuing flow of said cryogen through said apertures onto said tissue.

28. A probe of claim 13 wherein said elongated hollow tip includes at least one electro-surgical electrode.

29. A cryosurgical system of claim 20 wherein said electrical instruments for monitoring necrosis detect changes in impedance, said console includes a dispatcher/scanner electrically connected to said electrical instruments and said distal end of said tip to obtain electrical signals indicating a change in impedance, said electrical instruments for monitoring necrosis include at least one remote electrode adapted to be attached to the skin, a plurality of tissue sensors adapted to be inserted into the area adjacent the necrosis, said dispatcher/scanner obtaining said electrical signals from said electrical instruments and said distal end of said tip and said remote electrode.

* * * * *